(12) United States Patent
Herrero et al.

(10) Patent No.: US 11,262,754 B2
(45) Date of Patent: Mar. 1, 2022

(54) AUTOMATIC AUTONOMOUS DRIVING OF A VEHICLE

(71) Applicant: Bayerische Motoren Werke Aktiengesellschaft, Munich (DE)

(72) Inventors: Mariano Herrero, Wyckoff, NJ (US); Yang Li, West Caldwell, NJ (US)

(73) Assignee: Bayerische Motoren Werke Aktiengesellschaft, Munich (DE)

( * ) Notice: Subject to any disclaimer, the term of this patent is extended or adjusted under 35 U.S.C. 154(b) by 243 days.

(21) Appl. No.: 15/271,681

(22) Filed: Sep. 21, 2016

(65) Prior Publication Data
US 2018/0079413 A1  Mar. 22, 2018

(51) Int. Cl.
*G05D 1/08* (2006.01)
*G06Q 50/30* (2012.01)
(Continued)

(52) U.S. Cl.
CPC ........... *G05D 1/0088* (2013.01); *B60W 30/10* (2013.01); *B60W 50/14* (2013.01); *G06Q 10/00* (2013.01);
(Continued)

(58) Field of Classification Search
CPC combination set(s) only.
See application file for complete search history.

(56) References Cited

U.S. PATENT DOCUMENTS

| 8,855,847 B2 * | 10/2014 | Uehara | G01C 21/3691 701/25 |
| 8,880,270 B1 * | 11/2014 | Ferguson | B60W 30/00 701/23 |

(Continued)

FOREIGN PATENT DOCUMENTS

| CN | 201638053 U | 11/2010 |
| CN | 104054034 A | 9/2014 |

(Continued)

OTHER PUBLICATIONS

PCT/EP2017/072592, International Search Report (PCT/ISA/210 and PCT/ISA/220) dated Nov. 14, 2017, enclosing Written Opinion of the International Searching Authority (PCT/ISA/237) (Fifteen (15) pages).

(Continued)

*Primary Examiner* — Tyler J Lee
(74) *Attorney, Agent, or Firm* — Crowell & Moring LLP

(57) ABSTRACT

A motor vehicle includes a plurality of sensors, a wireless communication unit, and a control device that is configured to receive data from the plurality of sensors and via the wireless communication unit relating to at least one of an environmental condition, a mechanical condition and a health-rated condition. The control unit formats the received data into a predetermined format corresponding to at least one detected condition, and compares the at least one detected condition to a plurality of known conditions. The control unit is further configured to identify a detected known condition when the at least one detected condition matches at least one of the plurality of known conditions, to select, in response to identifying the detected known condition, an automatic autonomous driving mode of the vehicle, and then to execute a predetermined driving maneuver corresponding to the detected known condition.

18 Claims, 3 Drawing Sheets

(51) Int. Cl.
*G06Q 10/00* (2012.01)
*B60W 30/10* (2006.01)
*B60W 50/14* (2020.01)
*G05D 1/00* (2006.01)

(52) U.S. Cl.
CPC ....... *G06Q 50/30* (2013.01); *B60W 2510/244* (2013.01); *B60W 2530/00* (2013.01); *B60W 2530/209* (2020.02); *B60W 2540/22* (2013.01); *B60W 2540/26* (2013.01); *B60W 2552/00* (2020.02); *B60W 2554/00* (2020.02); *B60W 2555/20* (2020.02); *B60W 2556/45* (2020.02)

(56) References Cited

U.S. PATENT DOCUMENTS

| | | | |
|---|---|---|---|
| 9,494,935 | B2 | 11/2016 | Okumura et al. |
| 9,547,986 | B1* | 1/2017 | Curlander ................ G08G 1/04 |
| 9,805,519 | B2* | 10/2017 | Ramanujam ........... G07C 5/006 |
| 10,248,120 | B1* | 4/2019 | Siegel ................ G01C 21/3602 |
| 2014/0244096 | A1* | 8/2014 | An ........................ G05D 1/0055 |
| | | | 701/25 |
| 2014/0277894 | A1* | 9/2014 | Doyle ...................... G05D 1/00 |
| | | | 701/23 |
| 2014/0358353 | A1 | 12/2014 | Ibanez-Guzman et al. |
| 2015/0066282 | A1 | 3/2015 | Yopp |
| 2015/0241878 | A1 | 8/2015 | Crombez et al. |
| 2015/0293216 | A1* | 10/2015 | O'Dea .................... G01S 13/87 |
| | | | 701/23 |
| 2015/0348335 | A1* | 12/2015 | Ramanujam ........... G07C 5/006 |
| | | | 701/23 |
| 2016/0001781 | A1* | 1/2016 | Fung ...................... G06F 19/345 |
| | | | 701/36 |
| 2016/0167668 | A1* | 6/2016 | Prokhorov ...... B60W 30/18009 |
| | | | 701/23 |
| 2017/0213165 | A1* | 7/2017 | Stauffer ................. G06Q 10/02 |
| 2017/0228717 | A1* | 8/2017 | Rovik .................... G06Q 20/28 |
| 2017/0363432 | A1* | 12/2017 | Hall .................. G01C 21/3469 |

FOREIGN PATENT DOCUMENTS

| | | |
|---|---|---|
| DE | 10 2012 014 717 A1 | 1/2014 |
| DE | 10 2015 118 489 A1 | 5/2016 |
| JP | 2011-232815 A | 11/2011 |
| WO | WO 2015/200224 A2 | 12/2015 |

OTHER PUBLICATIONS

Chinese Office Action issued in Chinese application No. 201780045830.8 dated Apr. 6, 2021, with English translation (Sixteen (16) pages).

* cited by examiner

AUTOMATIC AUTONOMOUS DRIVING OF A VEHICLE

FIELD OF THE INVENTION

The invention relates to automatic autonomous driving of a vehicle and, more particularly, to automatic autonomous control of a vehicle without operator input that is carried out in response to a detected known condition.

BACKGROUND

Conventionally, driver assistance systems have been used in vehicles, such as for ascertaining the optimum route, speed and distance to a vehicle ahead, as lane departure warning systems, for overtaking maneuvers, for traveling along expressways, for parking and the like. All of these systems, however, require explicit input and monitoring from the driver, and therefore are not considered to be autonomous systems.

Recently, more advanced operator-based autonomous driving systems are currently under development in which vehicles are designed to autonomously travel to an operator-defined destination, or in accordance with some other operator input. Such a system is autonomous in the sense that, once the operator activates the system and provides instructions, the system is configured to maneuver the vehicle to the indicated destination without additional operator input and monitoring because the system is designed to detect the vehicle's surroundings using a variety of techniques, such as radar, lidar, GPS, odometry, and computer vision.

However, such operator-based autonomous driving systems are deficient because they still require operator input, meaning they are still limited by the operator's awareness of situations, reaction time and potentially incorrect responses. As such, there is a need in the art for a truly automatic autonomous system which maneuvers a vehicle, under certain known conditions, without any user input or direction.

It is therefore an object of the invention to provide an automatic autonomous system for operating a vehicle without any operator input.

SUMMARY OF THE INVENTION

In one embodiment of the invention, a motor vehicle includes a plurality of sensors, a wireless communication unit, and a control device, coupled to the plurality of sensors and wireless communication unit. The control device is configured to receive data from the plurality of sensors and via the wireless communication unit relating to at least one of an environmental condition, a mechanical condition and a health-rated condition. The control unit then formats the received data into a predetermined format corresponding to at least one detected condition, and compares the at least one detected condition to a plurality of known conditions. The control unit is further configured to identify a detected known condition when the at least one detected condition matches at least one of the plurality of known conditions, to select, in response to identifying the detected known condition, an automatic autonomous driving mode of the vehicle, and then to execute a predetermined driving maneuver corresponding to the detected known condition.

Other objects, advantages and novel features of the present invention will become apparent from the following detailed description of one or more preferred embodiments when considered in conjunction with the accompanying drawings.

DESCRIPTION OF EXEMPLARY EMBODIMENTS OF THE INVENTION

Figure 1:
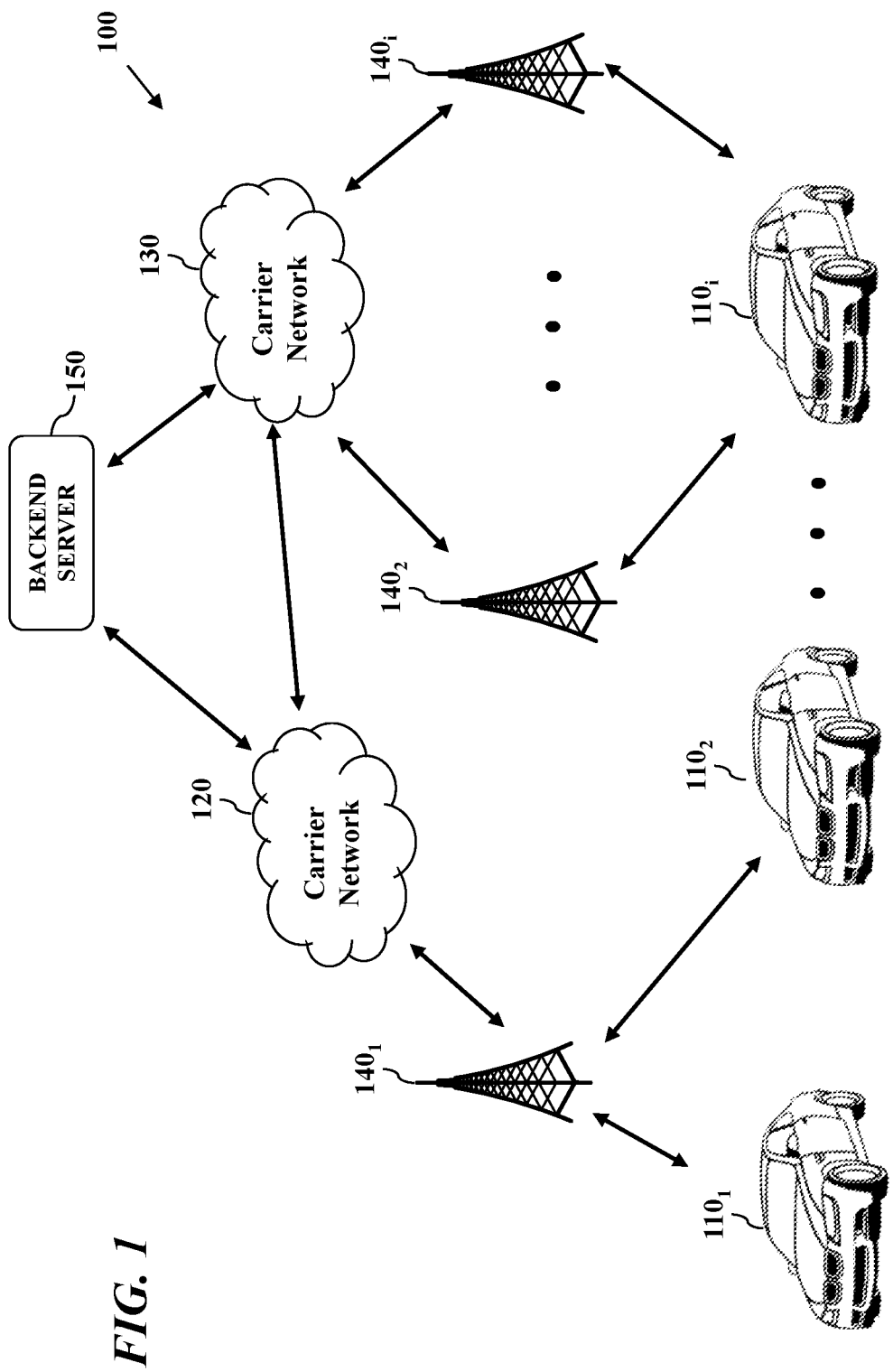
FIG. 1 illustrates one embodiment of a communication system configured to implement one or more aspects of the invention.

One aspect of the invention is a control device of a motor vehicle in which an evaluation unit of the control device is configured to process captured and/or received data as the basis for identifying and evaluating an environmental, mechanical or health-related condition that may require that an automatic autonomous driving mode be selected and that a predetermined maneuver be executed. The identification of known conditions, and the automatic selection of an appropriate driving mode and corresponding maneuver based thereon, reduces the danger of an unduly late or incorrect reaction to a suddenly changing situation and additionally relieves the burden on the driver.

As used herein, the terms "a" or "an" shall mean one or more than one. The term "plurality" shall mean two or more than two. The term "another" is defined as a second or more. The terms "including" and/or "having" are open ended (e.g., comprising). The term "or" as used herein is to be interpreted as inclusive or meaning any one or any combination. Therefore, "A, B or C" means "any of the following: A; B; C; A and B; A and C; B and C; A, B and C". An exception to this definition will occur only when a combination of elements, functions, steps or acts are in some way inherently mutually exclusive.

Reference throughout this document to "one embodiment", "certain embodiments", "an embodiment" or similar term means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner on one or more embodiments without limitation.

In accordance with the practices of persons skilled in the art of computer programming, the invention is described below with reference to operations that are performed by a computer system or a like electronic system. Such operations are sometimes referred to as being computer-executed. It will be appreciated that operations that are symbolically represented include the manipulation by a processor, such as a central processing unit, of electrical signals representing data bits and the maintenance of data bits at memory locations, such as in system memory, as well as other processing of signals. The memory locations where data bits are maintained are physical locations that have particular electrical, magnetic, optical, or organic properties corresponding to the data bits.

When implemented in software, the elements of the invention are essentially the code segments to perform the necessary tasks. The code segments can be stored in a processor readable medium or transmitted by a computer data signal. The "processor readable medium" may include any medium that can store information. Examples of the processor readable medium include an electronic circuit, a semiconductor memory device, a ROM, a flash memory or other non-volatile memory, a floppy diskette, a CD-ROM, an optical disk, a hard disk, etc.

The term "backend server" means a functionally-related group of electrical components, such as a computer system in a networked environment which may include both hardware and software components, or alternatively only the software components that, when executed, carry out certain functions. The "backend server" may be further integrated with a database management system and one or more associated databases.

The terms "environmental condition" or "environmental data" means a condition or data, respectively, that broadly relates to information external to the vehicle, including for example, information related to weather, proximity to external objects (e.g., vehicles, pedestrians, obstacles, etc.), date or time of day, accumulation of debris on the vehicle, traffic conditions, road construction and closures, a hazardous (e.g., fire, tornado, hurricane, earthquake, etc.), a crime in progress, riots, areas of known high crime, areas of known high vehicle accidents, information from environmental sensors, such as CO, $CO_2$, PM2.5, smoke, humidity, radiation sensors, etc.

The term "mechanical condition" or "mechanical data" means a condition or data, respectively, that broadly relates to the operation of the vehicle and/or the mechanics thereof, including for example, fuel level, oil level (or other liquid level), a vehicle malfunction, vehicle maintenance, vehicle inspection, battery charge status for e-vehicles, tire pressure, vehicle shape/size, etc.

The term "health-related condition" or "health-related data" means a condition or data, respectively, that broadly relates to the health of a person, such as a vehicle occupant, including for example, information relating to human vital signs, a heart attack, a stroke, an epileptic state, hyperthermia, hypothermia, hypoxia, drowsiness, or any health state which prevents the driver to operate the vehicle safely.

FIG. 1 illustrates a block diagram of a system 100 configured to implement one or more aspects of the invention. In one embodiment, the system 100 provides a wireless communication channel for cellular-capable vehicles, such as vehicles $110_1$-$110_i$ ("110"), which communicate with one or more carrier network 120 and 130 via a network of local base stations $140_1$-$140_i$ ("140") as the vehicles 110 move from having network coverage from one of the plurality of base stations 140 to another, or from one carrier network 120/130 to another. In addition, it should be appreciated that carrier networks 120 and 130 may be GSM, CDMA, etc., and may be accessible using a variety of access technologies, such as WiFi, Near Field Communication, satellite communication, Bluetooth, or any other wireless communication method using waves and/or particles.

The system 100 further comprises a backend server 150 that may be operated by or on behalf of one or more manufacturer(s) of vehicles 110. It should be appreciated that the backend server 150 may be implemented using a plurality of geographically dispersed servers, or may be implemented in a more centralized architecture.

Continuing to refer to FIG. 1, backend server 150 may be configured to communicate with the onboard computer systems of vehicles 110, and may particularly be configured to send and receive a variety of data/instructions to and from vehicles 100. By way of a non-limiting example, backend server 150 may be configured to receive and process sensor-based data that is collected by vehicles 110 and transmitted wirelessly to the backend server 150. Such sensor-based data may include environmental, mechanical or health-related data, as described in more detail below.

In addition, backend server 150 may be configured to collect and wirelessly transmit environmental data to the vehicles 110 for further processing in accordance with carrying out one or more aspects of the invention, as further detailed below.

Figure 2:
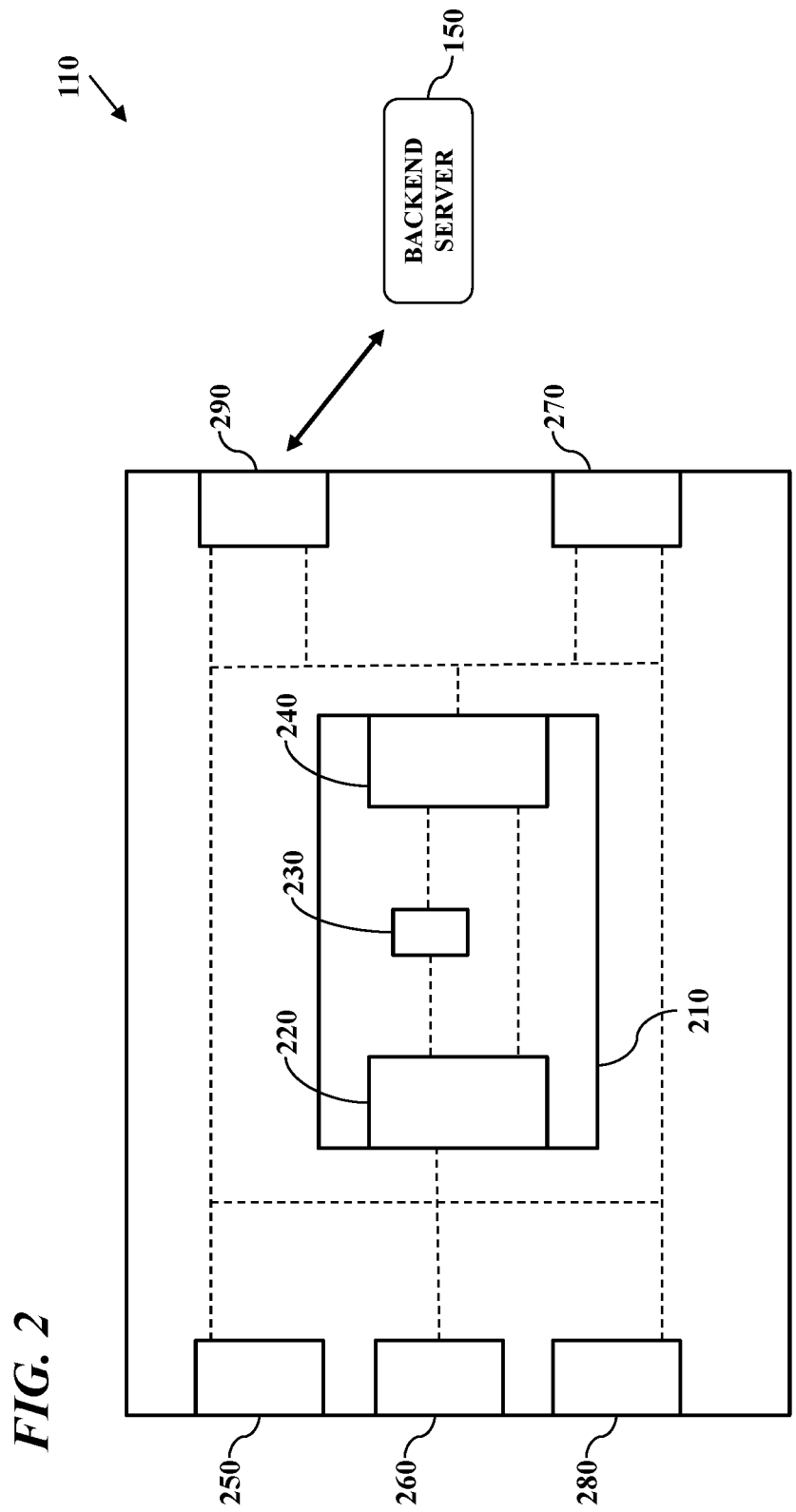
FIG. 2 illustrates a simplified schematic of an onboard vehicle system configured to carrying out one or more embodiments of the invention.

Referring now to FIG. 2, depicted is a simplified schematic of a vehicle 110. Vehicle 110 has a plurality of different sensor units 250, 260, 270, 280. Although only four sensor units are shown in FIG. 2 and described below, it should of course be appreciated that the vehicle 110 may be equipped with any number of known sensors. The dashed lines between the individual components in FIG. 2 represent data communication lines or data communication channels between the individual units.

With respect to the exemplary depicted sensors, an acoustic sensor unit 250 may be configured to receive sounds and audible signals. An audible signal may be, for example, a siren or an alarm, or the like. An optical sensor unit 260 can comprise a camera and/or an optical scanning system based on Lidar, for example. A radar unit 270 may be used to locate objects and to scan the environment surrounding the vehicle with microwaves, for example. An infrared unit 280 may be configured to detect infrared lightwaves reflected or transmitted by objects.

It should further be appreciated that the vehicle 110 may comprise other sensors, as noted above, including for example moisture sensors for sensing rain and snow conditions, temperature and smoke sensors, vibration and motion sensors, and any other known sensor relating to vehicle operation and/or vehicle mechanics (e.g., fuel level sensors, oil level sensors, tire pressure sensor, vehicle diagnostic sensors, vehicle maintenance sensors, etc.).

Although not shown, it should further be appreciated that the vehicle 110 may preferably be equipped with a geo-positioning system or other locating system or self-locating system, such as a Global Positioning System (GPS) or comparable system (e.g., GLONASS, GALILEO, etc.).

The vehicle 110 of FIG. 2 further comprises a wireless communication unit 290 for communication via radio signals, for example with backend server 150, as detailed above. It should further be appreciated that wireless communication unit 290 may enable the vehicle 110 to communicate with a control center, a rescue center or other vehicles.

Vehicle 110 additionally includes a control device 210 that comprises an evaluation unit 220. In certain embodiments, the control device 210 may comprise a part of the vehicle's onboard electrical system and may include one or more hardware modules comprised of conventional data processing units, such as logic circuits or microcomputers, or as reconfigurable memory units, such as Field Programmable Gate Arrays (FPGA). To that end, the evaluation unit 220 (as well as the other units comprising the control device 210 described below) may be implemented in hardware or software using one or more of such data processing units or FPGAs.

The evaluation unit 220 receives the sensor data captured by the sensor units 250, 260, 270, and 280 also received data such as data received via the wireless communication unit 290. This captured/received data, which may be received on a continuous or periodic basis, may also be processed using additional information stored in the vehicle's data memories or databases (not shown), which are generally known in the vehicular arts. In addition, the evaluation unit 220 may be configured to process the received or captured data by evaluating audible data, visual data, radio data, etc., using Doppler, traffic information and/or by evaluation of information from vehicle-to-vehicle and/or vehicle-to-infrastructure communications, which may be based on cellular and/or wireless LAN technology. It is thus possible to evaluate information of various complexities and from different sources, which may then be formatted in a predetermined format.

After the evaluation unit 220 evaluates the above captured/received data, which may be carried out on a continuous or periodic basis, it may generate and provide a corresponding mode signal to direct the selection unit 230 to select the vehicle's driving mode. The generation of the mode signal is described below in more detail with respect to FIG. 3. In any event, the selection unit 230 may be configured to select between a manual driving mode, a driver-based autonomous mode, and an automatic autonomous mode based on the mode signal received from the evaluation unit 220. In the manual driving mode, the vehicle is operated manually by the operator (e.g., the operator steers, brakes, accelerates), or with the assistance of conventional driver assistance systems (e.g., cruise control). In the driver-based autonomous mode, the operator provide an initial input/instruction for traveling to a desired destination, after which the vehicle travels to the indicated destination without further or with only minimal driver input. Finally, in the automatic autonomous mode that is the submit of the current invention, the vehicle initiates and executes a driving maneuver without any user input.

Alternatively, the selection unit 230 may be configured to only select between a non-automatic autonomous mode and an automatic autonomous mode, where the automatic autonomous mode is as described above and the non-automatic autonomous mode is a standard mode or any other operator-based mode.

As will be described in more detail below, the automatic autonomous mode can comprise the following special driving maneuvers and routines, for example: executing evasive action to avoid an errant vehicle, moving the vehicle into a nearby garage (e.g., in response to weather conditions), moving the vehicle out of a garage (e.g., in response to a fire or other hazardous situation), traveling to a repair shop (e.g., in response to overdue maintenance or critical malfunction, traveling to nearest or preferred gas station or charging station (e.g., in response to low fuel or charge level), traveling to nearby or preferred hospital or emergency center (e.g., in response to passenger health condition), traveling to a car wash if vehicle is dirty, traveling to pick up packages or other items such as groceries. These maneuvers are controlled automatically by the control device 210 without the driver needing to intervene in the control of the vehicle 110.

The selected driving mode is transmitted to the actuation unit 240. The actuation unit 240 actuates the corresponding functional elements of the vehicle 110, such as steering mechanism, brakes, the fuel metering ("gas"), actuation of an electric drive (in the case of electric and hybrid vehicles), a gear, the lighting installation and any and all other vehicle components and computational systems that are required for operation of the vehicle 110 in the selected driving mode. In the case of the automatic autonomous mode, the actuation unit 240 may be configured to access a database with a plurality of predetermined maneuvers that are designed to appropriately respond to the particular detected known condition, as described in more detail below.

Figure 3:
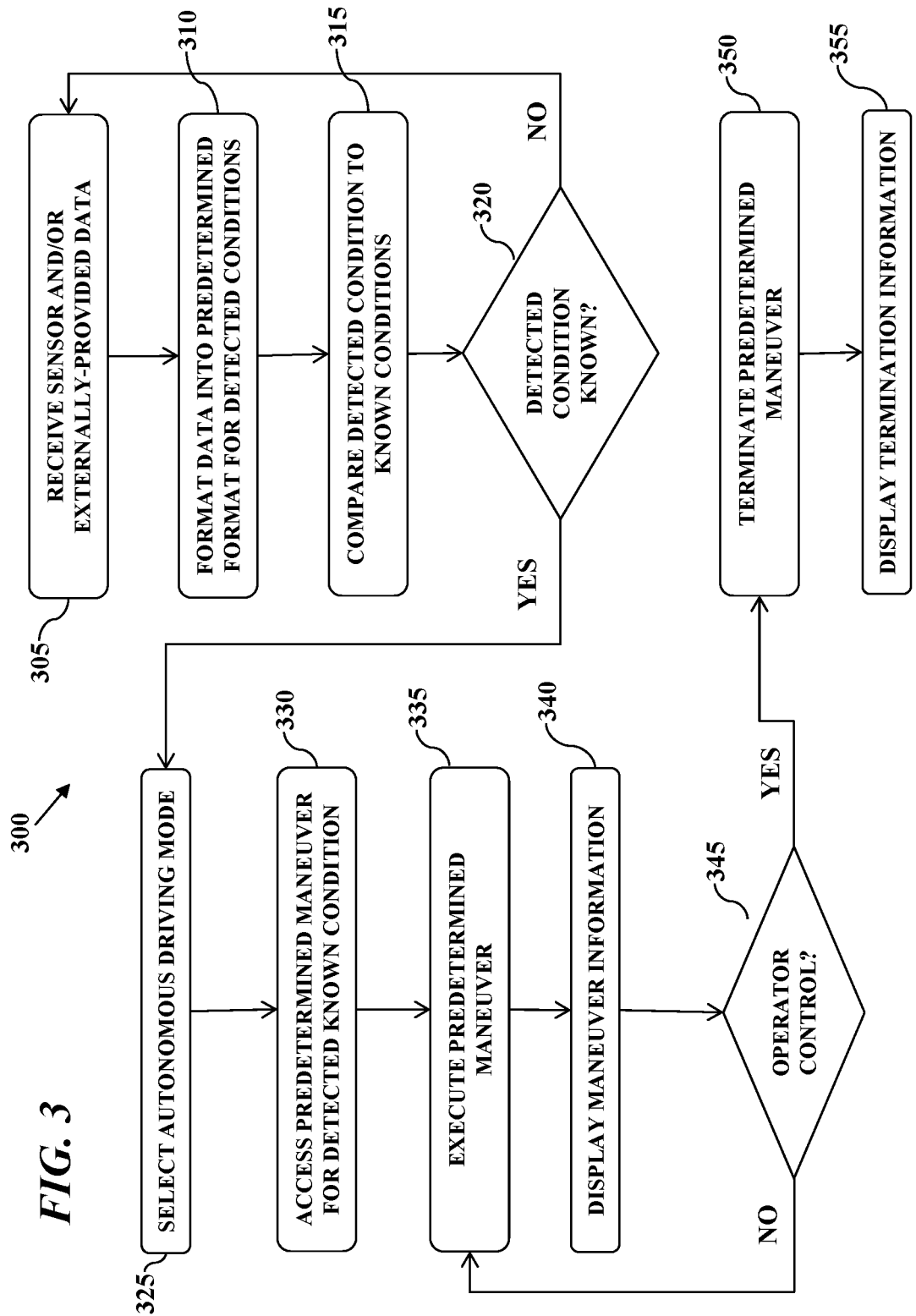
FIG. 3 illustrates a flow diagram for one embodiment of a process for carrying out the invention.

Referring now to FIG. 3, depicted is a flow diagram for one embodiment of a process for carrying out the invention. It is assumed that the vehicle is initially in a standard mode, i.e. in the manual mode or the operator-based autonomous mode. Process 300 then begins at block 305 with the receiving/capturing of sensor data and/or externally-provided data (e.g., received from a backend server) which, as noted above, may occur on a continuous or period basis. Such sensor data may include any sensor-provided data related to an environmental, mechanical and/or health-related condition, while the externally-provided data may also include data related to an environmental condition (e.g., traffic information, weather conditions, location of a hazard, traffic accident, crime in progress, etc.).

The received data of block 305 may then be formatted into a predetermined format corresponding to one or more detected conditions (block 310). It should be appreciated that the predetermined format may assume any form, so long as the chosen format is suitable for characterizing or otherwise being representative of the aforementioned environmental, mechanical and health-related conditions.

Once the data has been formatted so as to be representative of a detected condition, process 300 may then continue to block 315 where the detected condition(s) may be compared to known conditions. While the known conditions may be stored in a memory of the vehicle, they may also be stored in a remote database, such as part of backend server 150. In either case, the comparison operation of block 315 may be carried out in accordance with a template matching technique, by way of example only.

Process 300 continues to block 320 where a determination is made as to whether one or more of the detected conditions has been identified as being a known condition. If not, process 300 reverts to block 305 where sensor and externally-provided data is continually or periodically received and evaluated in accordance with the operations described above with reference to blocks 310 and 315.

If, on the other hand, it is determined at block 320 that a known condition has been detected, then process 300 may continue to block 325 where an automatic autonomous driving mode may be entered. In certain embodiments, the evaluation unit 220 of FIG. 2 described above may be configured to carry out the operations of blocks 310, 315 and 320, while the selection unit 230 may be configured to carry out the operation of block 325.

In any event, once the automatic autonomous mode is entered, process 300 may continue to block 330 where a response to the known condition is determined, such as by accessing a database with a plurality of predetermined maneuvers that are designed to appropriately respond to the particular detected known condition. For example, the predetermined driving maneuvers may be accessed from a computer memory of the vehicle from the backend server with which the vehicle is in wireless communication.

Once the appropriate predetermined maneuver has been accessed, it may be executed which, in certain embodiments, may comprise automatically carrying out one or more predefined driving maneuvers and routines, as noted above, such as executing evasive action to avoid an errant vehicle, moving the vehicle into a nearby garage (e.g., in response to weather conditions), moving the vehicle out of a garage (e.g., in response to a fire or other hazardous situation), traveling to a repair shop (e.g., in response to overdue maintenance or critical malfunction, traveling to nearest or preferred gas station or charging station (e.g., in response to low fuel or charge level), traveling to nearby or preferred hospital or emergency center (e.g., in response to passenger health condition), traveling to a car wash if vehicle is dirty, traveling to pick up packages or other items such as groceries.

While the maneuver to be carried out at block 335 is predetermined in the sense that the objective of the maneuver is predetermined and is carried out with no user input at all, the manner in which the objective is actually achieved will vary based on the location of the vehicle, its surroundings, and other environmental factors that may affect the ability of the vehicle to move in a particular direction or to operate at certain speeds. For example, executing a predetermined maneuver of exiting a parking garage in the event of a detected fire will require a mapping from the vehicle's current location to the nearest exit, as well as a consideration of identified vehicles and pedestrians that may be located along the way. However, since the ability to map a route to a determined destination, while avoiding obstacles along the way, is within the general field of autonomous vehicle operation, the present disclosure will not repeat that which is generally known with respect to autonomous vehicle operation.

When the predetermined maneuver relates to traveling to a destination, such as a hospital or emergency center in the case of a health-related condition, the manner in which this maneuver is carried out may preferably include searching for the closest appropriate medical facility, for example.

In certain embodiments, the operations of blocks 330 and 335 may be carried out by the actuation unit 240 of FIG. 1.

It should further be appreciated that the executing the predetermined maneuver may also include activating exterior signals (audible, visible, etc.) to alert other vehicles and pedestrians that an autonomous maneuver is being performed. Moreover, in the case of a maneuver in which the destination is a hospital or emergency center, the maneuver may further comprise establishing a voice and/or video call with the corresponding hospital to notify the center of the operator/occupant's arrival, as well as the transmission of relevant medical data to the hospital/emergency center (e.g., current vital signs, historical medical records, etc.).

Continuing to refer to FIG. 3, process 300 may also include providing information to the driver as to what maneuver or operation the vehicle is performing (block 340), such as by displaying the information to the driver either inside or outside the vehicle, sending push notifications to a mobile device or e-mail address containing a description, location of the event, destination and/or video signal from vehicle cameras. This may be advantageous so that the driver can re-acquire control of the vehicle if the driver deems the maneuver unnecessary or otherwise undesirable. To that end, the system may be programmed to continually monitor, during the execution of the maneuver, whether or not the vehicle operator has resumed control of the vehicle (block 345). In the event that there is a driver interruption of the maneuver, process 300 continues to block 350 where the maneuver is terminated. The displayed information relating to the predetermined maneuver being canceled may also be displayed to the driver (block 355).

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A motor vehicle comprising:
   a plurality of sensors;
   a wireless communication unit; and
   a control device, coupled to the plurality of sensors and wireless communication unit, wherein the control device is configured to:
      control the vehicle to drive in an autonomous driving mode and in a non-autonomous driving mode, wherein the autonomous driving mode is without user intervention;
      receive data from the plurality of sensors and via the wireless communication unit relating to at least one of an environmental condition, a mechanical condition and a health-related condition;
      format the received data into a predetermined format corresponding to at least one detected condition;
      compare the at least one detected condition to a plurality of known conditions;
      identify a detected known condition when the at least one detected condition matches at least one of the plurality of known conditions;
      select, without user input and in response to identifying the detected known condition, the automatic autonomous driving mode of the vehicle from among the autonomous driving mode and the non-autonomous driving mode;
      determine a destination corresponding to the detected known condition, in response to the selection of the automatic autonomous driving mode; and
      initiate, without user input, the automatic driving of the motor vehicle, via the automatic autonomous driving mode, to the determined destination, in response to the determination of the destination.

2. The motor vehicle as claimed in claim 1, wherein the at least one environmental condition comprises at least one of weather, proximity to an external object, date, time of day, an accumulation of debris on the motor vehicle, traffic conditions, road construction, a road closure, a hazard, a crime in progress, a riot, an area of known high crime, an area of known high vehicle accidents, and information from environmental sensors.

3. The motor vehicle as claimed in claim 1, wherein the at least one mechanical condition comprises at least one of fuel level, oil level, a vehicle malfunction, vehicle maintenance, vehicle inspection, a battery charge status, tire pressure, and a vehicle shape/size.

4. The motor vehicle as claimed in claim 1, wherein the at least one health-related condition comprises at least one of human vital signs, a heart attack, a stroke, an epileptic state, hyperthermia, hypothermia, hypoxia, drowsiness, and a health state that inhibits the driver from safely operating the vehicle.

5. The motor vehicle as claimed in claim 1, wherein the control device is configured to identify the detected known condition by performing a template matching operation using based on the at least one detected condition and the plurality of known conditions.

6. The motor vehicle as claimed in claim 1, wherein the control device is configured to cause the motor vehicle to automatically travel to the determined destination by one of moving the vehicle into or out of a garage, traveling to a repair shop, traveling to a gas station, traveling to hospital or emergency center, traveling to a car wash, traveling to a package pickup destination, and traveling to a merchant.

7. The motor vehicle as claimed in claim 1, wherein the control device is configured to cause the motor vehicle to automatically travel to the determined destination without any input from an operator of the vehicle.

8. The motor vehicle as claimed in claim 1, wherein, in determining the destination, the control device is configured to take into account a location of the vehicle and surroundings of the vehicle.

9. The motor vehicle as claimed in claim 1, wherein the control device is further configured to providing information to a driver of the motor vehicle corresponding to the determined information.

10. A method for automatically autonomously driving a motor vehicle comprising:
   receiving data from a plurality of sensors of the vehicle and via a wireless communication unit of the vehicle relating to at least one of an environmental condition, a mechanical condition and a health-related condition;
   formatting the received data into a predetermined format corresponding to at least one detected condition;
   comparing the at least one detected condition to a plurality of known conditions;
   identifying a detected known condition when the at least one detected condition matches at least one of the plurality of known conditions;
   selecting, without user input and in response to identifying the detected known condition, an automatic autonomous driving mode of the vehicle from among the autonomous driving mode and a non-autonomous driving mode, wherein the autonomous driving mode is without user intervention;
   determining a destination corresponding to the detected known condition, in response to the selection of the automatic autonomous driving mode; and
   initiating without user input, the automatic driving of the motor vehicle via the automatic autonomous driving mode to the determined destination, in response to the determination of the destination.

11. The method as claimed in claim 10, wherein the at least one environmental condition comprises at least one of weather, proximity to an external object, date, time of day, an accumulation of debris on the motor vehicle, traffic conditions, road construction, a road closure, a hazard, a crime in progress, a riot, an area of known high crime, an area of known high vehicle accidents, and information from environmental sensors.

12. The method as claimed in claim 10, wherein the at least one mechanical condition comprises at least one of fuel level, oil level, a vehicle malfunction, vehicle maintenance, vehicle inspection, a battery charge status, tire pressure, and a vehicle shape/size.

13. The method as claimed in claim 10, wherein the at least one health-related condition comprises at least one of human vital signs, a heart attack, a stroke, an epileptic state, hyperthermia, hypothermia, hypoxia, drowsiness, and a health state that inhibits the driver from safely operating the vehicle.

14. The method as claimed in claim 10, wherein identifying the detected known condition comprises performing a template matching operation using based on the at least one detected condition and the plurality of known conditions.

15. The method as claimed in claim 10, wherein causing the motor vehicle to automatically travel to the determined destination comprises one of moving the vehicle into or out of a garage, traveling to a repair shop, traveling to a gas station, traveling to hospital or emergency center, traveling to a car wash, traveling to a package pickup destination, and traveling to a merchant.

16. The method as claimed in claim 10, wherein causing the motor vehicle to automatically travel to the determined destination comprises causing the motor vehicle to automatically travel to the determined destination without any input from an operator of the vehicle.

17. The method as claimed in claim 10, wherein determining the destination corresponding to the detected known condition further comprises taking into account a location of the vehicle and surroundings of the vehicle.

18. The method as claimed in claim 10, further comprises displaying information, on a display in the vehicle, corresponding to the determined destination.

\* \* \* \* \*